United States Patent
Carvalho et al.

(10) Patent No.: US 8,746,045 B2
(45) Date of Patent: *Jun. 10, 2014

(54) SYSTEM AND METHOD FOR IDENTIFYING FLUIDS AND MONITORING FLUID QUALITY IN A VESSEL

(75) Inventors: Carlos E. Carvalho, Tyngsborough, MA (US); John L. Sinnamon, Deerfield, NH (US); Thomas Miskell, Merrimack, NH (US); Vincent J. Rizzo, Hollis, NH (US)

(73) Assignee: Meggitt (Orange County), Inc., Irvine, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 13/086,958

(22) Filed: Apr. 14, 2011

(65) Prior Publication Data
US 2011/0246100 A1  Oct. 6, 2011

Related U.S. Application Data

(63) Continuation-in-part of application No. 12/630,225, filed on Dec. 3, 2009, now Pat. No. 8,020,438, which is a continuation of application No. 11/650,841, filed on Jan. 8, 2007, now Pat. No. 7,650,785.

(60) Provisional application No. 60/859,756, filed on Nov. 17, 2006.

(51) Int. Cl.
*G01N 11/00* (2006.01)
*G01F 17/00* (2006.01)

(52) U.S. Cl.
USPC ............................................ 73/53.01; 702/50

(58) Field of Classification Search
USPC ......... 702/55, 159, 50; 73/23.2, 53.01, 290 V
See application file for complete search history.

(56) References Cited

U.S. PATENT DOCUMENTS

| 2,709,918 A | 6/1955 | Yetter |
| 3,394,589 A | 7/1968 | Genichiro |

(Continued)

FOREIGN PATENT DOCUMENTS

| DE | EP 1429125 | * | 6/2004 |
| EP | 0473082 A | | 3/1992 |

(Continued)

OTHER PUBLICATIONS

A. Cataldo, A. Lay-Ekuakille, C. Decarlo, Remote Sensing of Liquid Characteristics Using Time Domain Reflectometry, Earth Observing Systems VII, Proceedings of SPIE vol. 4814 (2002) p. 465-473, AGM Industrie S.p.A., Martignnano Lecce, Italy.

*Primary Examiner* — Hezron E Williams
*Assistant Examiner* — Nathaniel Kolb
(74) *Attorney, Agent, or Firm* — Peter A. Nieves; Sheehan Phinney Bass + Green PA

(57) ABSTRACT

Methods and systems are disclosed for using time domain reflectometry to determine the identity of a fluid in a vessel, and to determine whether the quality of a fluid in a vessel is within acceptable parameters. Methods include identifying a fluid by comparing a derived characteristic of a fluid to a reference characteristic, determining the quality of a fluid by determining if a derived characteristic is within an acceptable quality range, monitoring a fluid for a dynamic change in quality or state, and identifying a fluid by comparing a transition reflection waveform to a reference signature transition. The methods are implemented in systems for identifying a fluid layer in a vessel, such as fuel, free liquid water or ice, detecting misfueling or fuel contamination, and detecting fluid state changes, such as the formation of ice.

15 Claims, 6 Drawing Sheets

(56) References Cited

U.S. PATENT DOCUMENTS

| | | | |
|---|---|---|---|
| 3,824,597 A | 7/1974 | Berg | |
| 3,858,208 A | 12/1974 | Parke et al. | |
| 3,995,212 A | 11/1976 | Ross | |
| 4,042,925 A | 8/1977 | Albanese et al. | |
| 4,135,397 A | 1/1979 | Krake | |
| 4,499,466 A | 2/1985 | Torino, Jr. et al. | |
| 4,596,144 A | 6/1986 | Panton et al. | |
| 4,621,264 A | 11/1986 | Yashiro et al. | |
| 4,680,589 A | 7/1987 | Bryant et al. | |
| 5,014,011 A * | 5/1991 | Colvin | 324/663 |
| 5,374,931 A | 12/1994 | Wiener | |
| 5,457,990 A | 10/1995 | Oswald et al. | |
| 5,610,611 A | 3/1997 | McEwan | |
| 5,827,985 A | 10/1998 | Grieger et al. | |
| 5,841,666 A | 11/1998 | Perdue et al. | |
| 5,943,908 A | 8/1999 | Innes et al. | |
| 5,973,637 A | 10/1999 | Perdue et al. | |
| 6,078,280 A * | 6/2000 | Perdue et al. | 342/124 |
| 6,164,132 A * | 12/2000 | Matulek | 73/304 C |
| 6,229,476 B1 | 5/2001 | Lutke et al. | |
| 6,232,910 B1 | 5/2001 | Bell et al. | |
| 6,281,801 B1 | 8/2001 | Cherry et al. | |
| 6,556,511 B1 | 4/2003 | Welke | |
| 6,559,657 B1 | 5/2003 | McCarthy et al. | |
| 6,626,038 B1 | 9/2003 | Carsella et al. | |
| 6,640,629 B2 | 11/2003 | Carsella et al. | |
| 6,644,114 B1 | 11/2003 | McEwan | |
| 6,650,280 B2 | 11/2003 | Arndt et al. | |
| 6,690,320 B2 | 2/2004 | Benway et al. | |
| 6,867,729 B2 | 3/2005 | Berry et al. | |
| 6,906,662 B2 | 6/2005 | Faust et al. | |
| 7,068,051 B2 | 6/2006 | Anderson | |
| 7,073,379 B2 | 7/2006 | Schroth et al. | |
| 7,162,922 B2 | 1/2007 | Freger et al. | |
| 7,237,435 B2 | 7/2007 | Motzer et al. | |
| 7,243,539 B2 | 7/2007 | Otto et al. | |
| 7,392,699 B2 | 7/2008 | Motzer et al. | |
| 7,446,695 B2 | 11/2008 | McEwan | |
| 7,525,476 B1 | 4/2009 | Delin et al. | |
| 7,571,645 B2 | 8/2009 | Bostrom | |
| 2002/0084931 A1 | 7/2002 | Bletz | |
| 2002/0101373 A1 | 8/2002 | Arndt et al. | |
| 2002/0125899 A1 * | 9/2002 | Lvovich et al. | 324/698 |
| 2003/0016030 A1 * | 1/2003 | Schwartz et al. | 324/670 |
| 2004/0007061 A1 | 1/2004 | Forgue | |
| 2004/0182149 A1 | 9/2004 | Balin et al. | |
| 2004/0183550 A1 | 9/2004 | Fehrenbach et al. | |
| 2005/0127924 A1 | 6/2005 | Motzer et al. | |
| 2005/0192727 A1 | 9/2005 | Shostak et al. | |
| 2007/0081617 A1 | 4/2007 | Fudge | |
| 2007/0204689 A1 | 9/2007 | Bostrom | |
| 2008/0034863 A1 | 2/2008 | Bartoli et al. | |
| 2008/0105048 A1 | 5/2008 | Nilsson et al. | |
| 2009/0076744 A1 | 3/2009 | Anderson | |
| 2009/0158839 A1 | 6/2009 | Spanke et al. | |
| 2009/0178478 A1 | 7/2009 | Reimelt et al. | |
| 2009/0249870 A1 | 10/2009 | Volpe et al. | |
| 2009/0282911 A1 | 11/2009 | Bostrom | |
| 2010/0000316 A1 | 1/2010 | Fehrenbach et al. | |
| 2010/0070208 A1 | 3/2010 | Sai | |
| 2010/0139393 A1 | 6/2010 | Miskell et al. | |
| 2010/0153029 A1 | 6/2010 | Miskell et al. | |

FOREIGN PATENT DOCUMENTS

| | | |
|---|---|---|
| WO | 9619715 A | 6/1996 |
| WO | 9926080 A | 5/1999 |
| WO | 2009046103 A | 4/2009 |

* cited by examiner

SYSTEM AND METHOD FOR IDENTIFYING FLUIDS AND MONITORING FLUID QUALITY IN A VESSEL

CROSS-REFERENCE TO RELATED APPLICATION

This application is a continuation-in-part of, and claims priority to, copending U.S. nonprovisional patent application entitled "Scan Lock and Track Fluid Characterization and Level Sensor Apparatus and Method," having Ser. No. 12/630,225, filed Dec. 3, 2009, which claims priority to U.S. Pat. No. 7,650,785, filed Jan. 8, 2007, which claims priority to U.S. Provisional Application Ser. No. 60/859,756, filed Nov. 17, 2006, each of which are hereby incorporated herein by reference in their entirety.

FIELD OF THE INVENTION

This invention relates to methods and systems for monitoring fluids in containers. In particular, this invention relates to methods and systems for identifying fluids, measuring and monitoring fluid quality in fuel tanks.

BACKGROUND OF THE INVENTION

Detecting physical properties of fluids in a vessel is important for a variety of reasons. Many applications, for example, marine and aviation applications, ground based vehicles, vessels and industrial processes require accurate measurements of fuel in a tank to ensure sufficient supplies to reach intended destinations. It is exceptionally important in aviation applications to monitor the fuel levels in multiple tanks to ensure proper balance of levels to impart the least impact on the aerodynamics of an aircraft, which can be significantly affected by changes in the three-dimensional center of gravity of a plane.

An accurate, reliable and safe method of measuring the amount of fluid in a container is essential. Present applications include fuel tanks containing volatile fluids, although the invention described herein can accommodate a wide range of fluids, regardless of their volatility characteristics. Other parameters that must be ascertained with accuracy and consistency are the type of fuel and the contamination content, if any. A further consideration is a need for hardware that meets the electromagnetic interference (EMI), electrostatic discharge (ESD) and interface requirements of a container, such as an aviation fuel tank, in its environment in a safe manner.

Prior radar technology includes methods to scan, lock on and track targets. The basic approach is to transmit a signal that, using radar terms, illuminates targets, performs gating on a receiver to locate targets and, optionally, selects targets to lock onto and track. Analysis of the received signal can then be used to determine the distance (range) of the target and to perform signature recognition to define the type of target and its characteristics. Combining radar technology with transmission line theory solves the problems attendant with sensing fluid levels in containers, particularly those used in the aviation field.

Time Domain Reflectometry (TDR) combines elements of radar technology with digital signal processing. A description of using TDR to detect fluid levels in a vessel is disclosed in the parent application, copending U.S. nonprovisional patent application entitled "Scan Lock and Track Fluid Characterization and Level Sensor Apparatus and Method," having Ser. No. 12/630,225, filed Dec. 3, 2009.

TDR combines elements of radar technology with digital signal processing. The radar component involves generating a signal, sometimes called an "interrogation pulse," and transmitting that signal into a vessel, for example, a fuel tank. An interrogation pulse may be, for example, a unit impulse, or a unit step function. The interrogation pulse may be transmitted with a waveguide, for example, a transmission line, a coaxial cable or a coaxial probe. The propagation speed of the interrogation pulse through a material is directly related to the relative permittivity (dielectric constant) of a material. Materials with different dielectric constants will have different propagation speeds. The transit time of the pulse is used to measure the dielectric constant. The propagation speed of the interrogation pulse depends upon the properties of the medium it is traveling through, according to the relationship demonstrated by the equation $$v = \frac{c}{\sqrt{\varepsilon}} \quad \text{(Eq. 1)}$$

where v=velocity of propagation, c=speed of light, and $\varepsilon$=the dielectric constant. The dielectric constant varies depending on material, and the dielectric constant of many materials can be a strong function of density (and thus of temperature), and is often a strong function of the amount of any additive or contaminant that may be present. Therefore, the velocity of propagation of the traveling pulse is in general changing as it goes from one material to another, and the velocity of propagation in any given medium may moreover vary in correspondence to such factors as additive content and temperature. The effect of temperature on the dielectric constant is especially true of liquids, and the effect of additive content on the dielectric constant is especially true of ethanol additive in hydrocarbon fuel.

Digital signal processing may be used to assist the resolution of the multiple reflected interrogation pulses. Generally, under the Nyquist theory, a waveform must be sampled at least at twice the highest frequency component of the waveform. But due to the combination of the high propagation speeds of the interrogation pulse and the short distances traveled by the interrogation pulses (typically the distance from the top of a fuel tank to the bottom of a fuel tank, and back), the sampling frequency must be extremely high. TDR takes advantage of the fact that the contents of the vessel being monitored change very slowly in relation to the propagation time of the interrogation pulse. Therefore, the reflection of a first interrogation pulse will be, for all practical purposes, indistinguishable from the reflection of a second interrogation pulse transmitted, for example, several nanoseconds later. This obviates the need to sample the received reflected impulse at the Nyquist frequency (twice the frequency of the highest component frequency present in the sampled waveform).

Instead of sampling an entire received waveform at the Nyquist frequency, TDR creates a "time expanded" composite of a sampled waveform by accumulating one or more samples of each reflected impulse. In order to create the composite, the delay between the transmitted pulse and the instant a sample is collected is progressively swept, so that the time difference between successive samples is less than or equal to the period corresponding to the Nyquist frequency. There is no objection to sampling at a higher frequency (for instance, collecting two or more samples for every interrogation pulse). The composite may be created by superimposing samples collected over multiple interrogation pulses. The operation on the sampled signal may then be performed by the signal processing circuitry as if the composite represented a single reflected waveform sampled at or above the Nyquist frequency.

The relatively low sampling frequency reduces the processing load on the signal processing circuitry, and similarly, allows the signal processing to be performed by lower speed and lower cost components. The processing load can be further reduced by only sampling the reflected waveform at selective times. For instance, there may be little interest in analyzing the portion of the reflected waveform corresponding to the reflections generated by impedance transitions that occur before the interrogation pulse enters the vessel, such as the point where the signal is transitioning from the transmission cable to the waveguide. Therefore the sampling time window may be restricted so that the received waveform consists of only reflections from a region of interest, such as the portion of a fuel tank containing fuel.

Where a plurality of stratifying fluids is present within a tank, it may furthermore be desirable to know the height of each stratified fluid layer. For example, where water is mixed with hydrocarbon fuel intentionally, such as when seawater is used as ballast in oil tankers; or unintentionally, such as when water is present in a vehicle fuel tank or such as when groundwater seeps into tanks for fuel pumps at filling stations or due to condensation, it may be desired to know the height of fuel layer(s) as distinct from nonfuel layer(s) for accurate determination of remaining fuel. The detection and measurement of stratified fluid layers is discussed in copending U.S. nonprovisional patent application entitled "System and Method for Optimizing Sweep Delay And Aliasing For Time Domain Reflectometric Measurement of Liquid Height Within A Tank," having Ser. No. 12/630,305, filed Dec. 3, 2009, which is hereby incorporated herein by reference in its entirety.

Another important measurement function is to ascertain the presence of, and/or amount of, any contaminants in fuel to ensure the safe and proper operation of engines operated with the fuel. Entry of contaminants into an operating engine can lead to severe performance problems and even engine failure. A means to constantly monitor the presence and amount of contaminants, particularly water and ice, is an important component of a fuel measurement system.

Water may be present in an aircraft fuel tank in several forms. Depending upon the form it takes, water can represent different problems to the operation of an aircraft. Water may be dissolved in another fluid, emulsified with an immiscible fluid, or free water may collect and form a water layer. In addition, depending upon the temperature, water may be present as an ice layer or as an ice-fuel mixture, forming a gel like substance. Water may be introduced to a fuel tank in different ways. Water may enter an aircraft fuel tank in the form of water vapor introduced through vents in fuel tanks, or may be introduced to the vehicle in the fuel itself as a solution. Water can accumulate and freeze, clogging fuel tanks and fuel lines. It is standard procedure in some aircraft to routinely check for the presence of water in a fuel tank after a certain time of flight.

A water mixture may exist in fuel in two states: dissolved water (single phase) or emulsified water (two phase). The amount of water present in fuel depends on the fuel grade and the fuel temperature. When water is dissolved it becomes part of the solution based on water molecule bonding, so it is impractical to remove. A small amount of dissolved water is normally found in fuel.

An emulsion is a mixture of two or more immiscible fluids, that is, a mixture of two or more fluids that are unblendable. A first fluid is dispersed in a second fluid, where the second fluid is in a continuous phase. The first fluid is said to be in a dispersed phase. The boundary between the dispersed phase and the continuous phase is called the interface. Emulsions generally appear cloudy or hazy, because the phase interfaces tend to scatter light. Fuel tanks in aircraft are constantly agitated, for example, by pumps, turbulence, and motion of the aircraft. This agitation may not allow emulsified water in fuel to separate and settle. If the temperature drops when, for instance, the aircraft climbs in altitude, the emulsified water may start to freeze, causing the fuel to gel.

Dissolved or emulsified water has traditionally been detected in fuel with chemical test kits. This typically involves taking a sample of fuel, adding water sensitive powder, and looking for a change of color. Then the color of the fuel is compared to a standard color card to determine if water is present.

Free water describes liquid water that is not in a dissolved or emulsified state. Free water generally settles as a stratified layer at the bottom of a tank, below the fuel. For general aviation craft, that is, small, generally propeller driven aircraft, the simplest method for detecting free water in fuel is a manual check before takeoff. A device is inserted into a valve at the bottom of the fuel tank that draws some fuel from the bottom of the tank. A fuel sample is drawn from the bottom of the tank because water is denser than fuel and therefore settles at the bottom of the tank. Once the sample is drawn, the pilot visually inspects the fuel sample for water. The water appears as clear bubbles or droplets. The fuel is usually dyed a color, which makes water bubbles visually distinguishable from the fuel. If water is detected, more fuel is drained from the bottom of the tank, and then another sample is again visually inspected. This process is repeated until the sample appears free from water. However, this process does not detect water that may be emulsified and thereafter settles out during flight, or water introduced to the fuel during flight.

Larger aircraft may have built-in water detecting systems. However, existing water detecting systems may not be accurate in many scenarios and may not be able to determine the amount of fluid in stratified layers, and further not be able to track or detect changes in fluid characteristics. Also, most current water detecting devices may not be able to detect or differentiate water from ice. While there are existing methods of water detection in aircraft, it is important to have redundant backup systems. Therefore, it is desirable for the fuel level detecting system to also detect free water or ice, as well as contamination in fuel. However, a capacitance probe, which has traditionally been used to detect fluid levels in tanks, cannot measure the impedance across two or more stratified layers of a tank. If the capacitance probe crosses a layer boundary, the resulting reported impedance will be a value somewhere between the impedance of each layer. So a capacitance probe is particularly ill suited for simultaneously detecting the fuel level and for detecting free water in a tank. For this reason, capacitance probes are often deployed so that they do not extend into the bottom inch or two of a fuel tank, where water is most likely to accumulate. Therefore, there is a need for a fuel level detector to monitor fuel quality in real time and to detect water and other contaminants.

SUMMARY OF THE INVENTION

A first aspect of the invention is a method of determining the identity of a fluid in a vessel, having the steps of transmitting an interrogation pulse into a vessel containing a fluid, receiving a first reflection of the interrogation pulse off of a first transition boundary, and receiving a second reflection of the interrogation pulse off of a second transition boundary.

Other steps include measuring the time between receiving the first reflection and receiving the second reflection, and calculating a derived characteristic of the fluid located between the first transition boundary and the second transition boundary based upon the time between receiving the first reflection and receiving the second reflection. A further step is comparing the derived characteristic of the fluid to a reference characteristic.

The reference characteristic of the first aspect may be selected as a function of temperature, the derived characteristic of the fluid may be the dielectric constant of the fluid, and the reference characteristic may be the dielectric constant of a reference fluid. Similarly, the derived characteristic of the fluid may be the propagation velocity of an electromagnetic pulse in the fluid, and the reference characteristic may be the propagation velocity of an electromagnetic pulse in a reference fluid. The derived characteristic of the fluid may be the impedance characteristics of the fluid, and the reference characteristic may be the impedance characteristics of a reference fluid. The steps of transmitting an interrogation pulse, receiving a first and second reflection of the interrogation pulse may be performed using time domain reflectometry. The derived characteristic may be normalized according to a reference temperature.

A second aspect of the invention is a method of detecting the quality of a fluid in a vessel, having the steps of transmitting an interrogation pulse into a vessel containing a fluid, receiving a first reflection of the interrogation pulse off of a first transition boundary, and receiving a second reflection of the interrogation pulse off of a second transition boundary. Further steps include measuring the time between receiving the first reflection and receiving the second reflection, and calculating a derived characteristic of the fluid located between the first transition boundary and the second transition boundary based upon the time difference between receiving the first reflection and receiving the second reflection. Additional steps include setting a quality floor threshold, setting a quality ceiling threshold, and determining whether the derived characteristic is between the quality floor threshold and the quality ceiling threshold.

In the second aspect of the invention, the steps of transmitting an interrogation pulse, receiving a first and second reflection of the interrogation pulse may be performed using time domain reflectometry. The step of setting the quality ceiling threshold may be a function of the temperature of the fluid in the vessel, and the step of setting the quality floor threshold may be a function of the temperature of the fluid in the vessel. The derived characteristic of the fluid may be the dielectric constant of the fluid, may be the propagation velocity of an electromagnetic pulse through the fluid, or may be the impedance characteristics of the fluid. The quality being detected may be a level of contamination, and the contamination may be emulsified water. Alternatively, the quality being detected may be the result of misfueling, or the presence of excessive additives.

A third aspect of the invention is a method of detecting a change in a fluid in a vessel, having the steps of measuring a fluid characteristic with TDR at a first time, measuring the fluid characteristic with TDR at a second time (where the second time is after the first time), and comparing the fluid characteristic measured at the first time to the fluid characteristic measured at the second time.

In the third aspect of the invention, further steps may include recording a first temperature of the fluid at the first time and recording a second temperature of the fluid at the second time. Additional steps may include calculating a normalized fluid characteristic at the first time by adjusting the fluid characteristic at the first time in relation to a reference temperature, calculating a normalized fluid characteristic at the second time by adjusting the fluid characteristic at the second time in relation to a reference temperature, and comparing normalized fluid characteristic at the first time to the normalized fluid characteristic at the second time. The fluid characteristic may be the dielectric constant, the velocity of propagation, impedance characteristics, or the number of detected transition boundaries. If the number of detected transition boundaries has changed, another step may be determining the identity of a fluid.

A fourth aspect of the invention is a method of determining the identity of a fluid in a vessel, having the steps of transmitting an interrogation pulse into a vessel containing a fluid, receiving a reflection of the interrogation pulse off of a transition boundary, characterizing the properties of the reflection, where the properties comprise polarity, slope, phase, and amplitude; and comparing the properties of the reflection to a reference boundary transition signature. The reference boundary transition signature may be an entry in a boundary transition signature table. A further step may include assigning a correlation value to the reflection of the interrogation pulse and the signature boundary transition.

Other systems, methods, features, and advantages of the present invention will become apparent to one with skill in the art upon examination of the following drawings and detailed description. It is intended that all such additional systems, methods, features and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

DEFINITIONS

As used within this specification and claims, "fluid" may refer to a substance in a gaseous or liquid state. Further, fluid may refer to a substance transitioning from liquid to ice, and a substance transitioning from ice to liquid.

As used within this specification and claims, a "transition boundary" is defined as a location that causes at least a portion of a transmitted interrogation pulse to reflect back toward the transmitter. A transition boundary may be the location of a transition between two different materials. These two materials may be two fluids, for example, air and fuel. Alternatively, the first material may be a fluid, and the second material may be a solid. For example, the first fluid may be fuel, and the second material may be ice. A transition boundary may also be a portion of the interrogation pulse transmitter that generates a reflection, such as the beginning or end of a probe or waveguide.

As used herein, a derived characteristic of a fluid is a characteristic, such as a physical property, that may be calculated from measured characteristics of the time of flight of an interrogation pulse through a fluid. The time it takes an interrogation pulse to traverse a fluid between a first transition boundary and a second transition boundary is such a measured characteristic. Examples of derived characteristics include velocity propagation, impedance, and the relative permittivity, often referred to as the dielectric constant.

As used herein, a reference characteristic is a physical property, such as density, temperature, impedance, and propagation velocity, among others, of a known reference fluid.

DETAILED DESCRIPTION

The present description describes in detail using TDR to determine the identity of a fluid in a vessel, and to determine whether the quality of a fluid in a vessel is within acceptable parameters. The following describes embodiments of methods for identifying a fluid by comparing a derived characteristic of a fluid to a reference characteristic, determining the quality of a fluid by determining if a derived characteristic is between a quality floor threshold and a quality ceiling threshold, monitoring a fluid for a dynamic change in quality, and identifying a fluid by comparing a transition reflection waveform to a reference signature transition.

It should be noted, that the present invention is not limited to the above mentioned use. These methods are illustrated through discussion of exemplary applications, including identifying a fluid layer in a vessel, such as fuel, free liquid water or ice, detecting misfueling or contamination, and detecting state changes in a fluid, such as the formation of ice. The present invention is not limited to these exemplary applications.

Time Domain Reflectometry

Figure 1:
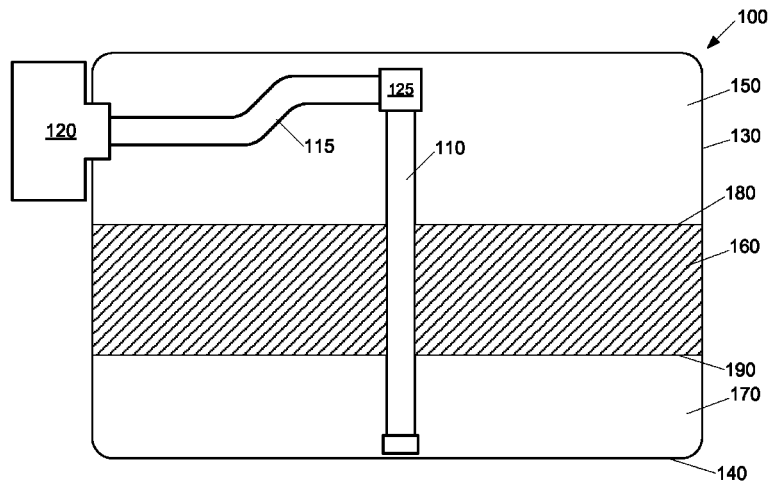
FIG. 1 is a diagram depicting portions of a TDR fluid sensing system for a vessel containing stratified fluids.

An example of a TDR fluid sensing system 100 is shown in FIG. 1. A probe 110 connected to a sensor 120 is located inside a vessel 130. The vessel 130 contains a first fluid 150, a second fluid 160 and a third fluid 170. In this example, the fluids 150, 160, and 170 are stratified in layers. For example, the first fluid 150 may be air, the second fluid 160 may be fuel, such as avgas (aviation gasoline, a high octane fuel used in aircraft using piston or Wankel engines, as distinguished from motor gasoline, or mogas), jet fuel, gasoline or oil, and the third fluid 170 may be, for example, water. The first fluid 150 is bounded at the top by vessel 130, and is bounded at the bottom by a first transition boundary 180, which marks the transition between the first fluid 150 and the second fluid 160. The second fluid 160 is bounded at the top by the first transition boundary 180, and at the bottom by a second transition boundary 190. The second transition boundary 190 separates the second fluid 160 from the third fluid 170. The third fluid 170 is bounded at the top by the second transition boundary 180 and the vessel bottom 140.

The probe 110 may be a coaxial probe, and may be perforated to allow entry of fluids 150, 160 and 170. The first transition boundary 180 and the second transition boundary 190 persist inside the probe 110. In contrast, an optional probe arm 115, which may connect the probe 110 to the sensor 120, may be filled with a solid dielectric, such as Teflon, or contain a coaxial interconnecting cable. Please note that while FIG. 1 depicts a TDR fluid sensing system 100 having a probe 110 connected to a probe arm 115 at a connection point 125, it is to be understood that other probe types and configurations are to be considered within the scope of this disclosure. For example, in some systems there may be no probe arm 115, so that the sensor 120 may connect directly to probe 110. Similarly, the sensor 120 may be connected to probe 110 through multiple connecting elements, including, but not limited to, coaxial cables or dielectric filled arms.

In the example of the TDR fluid sensing system 100, the sensor 120 transmits an interrogation pulse, which travels first through the probe arm 115 and into the probe 110. As the interrogation pulse encounters transitions between media, for example, the first transition boundary 180 between the first fluid 150 and the second fluid 160, or the second transition boundary 190 between the second fluid 160 and the third fluid 170, a portion of the interrogation pulse is transmitted, and a portion of the interrogation pulse is reflected back to the sensor 120. A receiver, which in this case is located in the sensor 120, receives these reflections. Similarly, the interrogation pulse may reflect off of physical surfaces, such as transitions in the transmission path. One example of a transition in the transmission path is the connection point 125 between the probe arm 115 and the probe 110. The receiver in the sensor 120 therefore may receive a composite of pulses reflected from each of these transition points. This composite received waveform is then analyzed to resolve and distinguish the individual reflections from the composite of reflected pulses at the receiver. Note, that while FIG. 1 depicts a coaxial probe that physically extends into fluids in a vessel, the TDR techniques described here are equally applicable to systems using other types of fluid sensing apparatus, for example antennas, horns, or waveguides.

The TDR apparatus and techniques described in and referenced by this disclosure are not intended to restrict the scope of this disclosure. The methods described are applicable to other techniques and devices used to measure the time difference between reflections of an interrogation pulse off of a first boundary transition and a second boundary transition regardless of the specific transmitting or receiving apparatus or sampling techniques employed.

Figure 2:
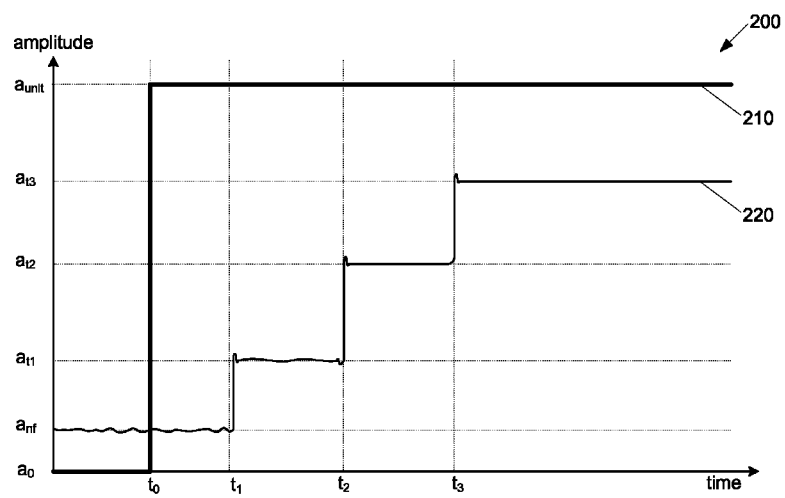
FIG. 2 is a representative amplitude-versus-time trace such as might be obtained from a TDR probe immersed in a vessel containing multiple fluid layers.

FIG. 2 is a timing diagram 200 indicating the relative timing and amplitude of an idealized interrogation pulse and the received reflected waveform in the example TDR system 100 of FIG. 1. The vertical axis of the timing diagram 200 represents signal amplitude, and the horizontal axis represents time. The timing diagram 200 shows the superposition of a transmitted interrogation pulse 210 and a received reflected waveform 220, as measured at the sensor 120 (FIG. 1). The interrogation pulse 210 represents the amplitude at the transmitter. The interrogation pulse 210 is represented as a unit step function, beginning with an amplitude of $a_0$ and rising to a unit amplitude $a_{unit}$ at time $t_0$. Excluding any transition at the connection point 125 for simplicity, the reflected waveform 220 represents the amplitude of the energy of the interrogation pulse 210 reflected back to the sensor 120 (FIG. 1) from first transition boundary 180 (FIG. 1), second transition boundary 190 (FIG. 1) and the end of the probe 110 (FIG. 1). Initially, the reflected waveform 220 has a low, but nonzero amplitude $a_{nf}$. This represents the noise floor at the receiver before a reflected waveform is received. At time $t_1$, the amplitude rises, oscillating somewhat before settling at amplitude $a_{r1}$. This represents the detection of the interrogation pulse 210 off of the first transition boundary 180 (FIG. 1). The difference between time $t_1$ and time $t_0$ represents the time for the interrogation pulse to leave the transmitter at sensor 120 (FIG. 1), arrive at the first transition boundary 180 (FIG. 1) and to reflect back to the receiver at sensor 120 (FIG. 1).

At time $t_2$, the amplitude rises, oscillating somewhat before settling at amplitude $a_{r2}$. This represents the time when the receiver detected the reflection of interrogation pulse 210 off of the second transition boundary 190 (FIG. 1). Note that the amplitude at time $t_2$ represents the aggregate of the reflection from the first transition boundary 180 (FIG. 1) and the second transition boundary 190 (FIG. 1). The time it took the leading edge of interrogation pulse 220 to traverse the layer containing the second fluid 160 (FIG. 1) may be calculated by subtracting $t_1$ from $t_2$.

Similarly, $a_{r3}$ represents the amplitude of the reflected signal at time $t_3$, which in this example represents the time of reception of the reflection off of the bottom of the probe 110 (FIG. 1). As above, $t_3-t_2$ represents the time it took for the interrogation pulse to traverse the layer containing the third fluid 170 (FIG. 1). The velocity of propagation, v, of the interrogation pulse 210 in the layer containing fluid 170 is given by equation 2, $$v = \frac{d}{t3 - t2} \quad \text{(Eq. 2)}$$

where v is the velocity of propagation, and d is the distance between the second transition boundary 190 (FIG. 1) and the bottom of the probe 110 (FIG. 1).

Note the diagram of FIG. 2 is simplified somewhat for purposes of illustration. It does not include reflections from other transition boundaries that may be present in the transmission system, such as when the interrogation pulse traverses the connection point 125 between the probe arm 115 (FIG. 1) and the probe 110 (FIG. 1).

Figure 3:
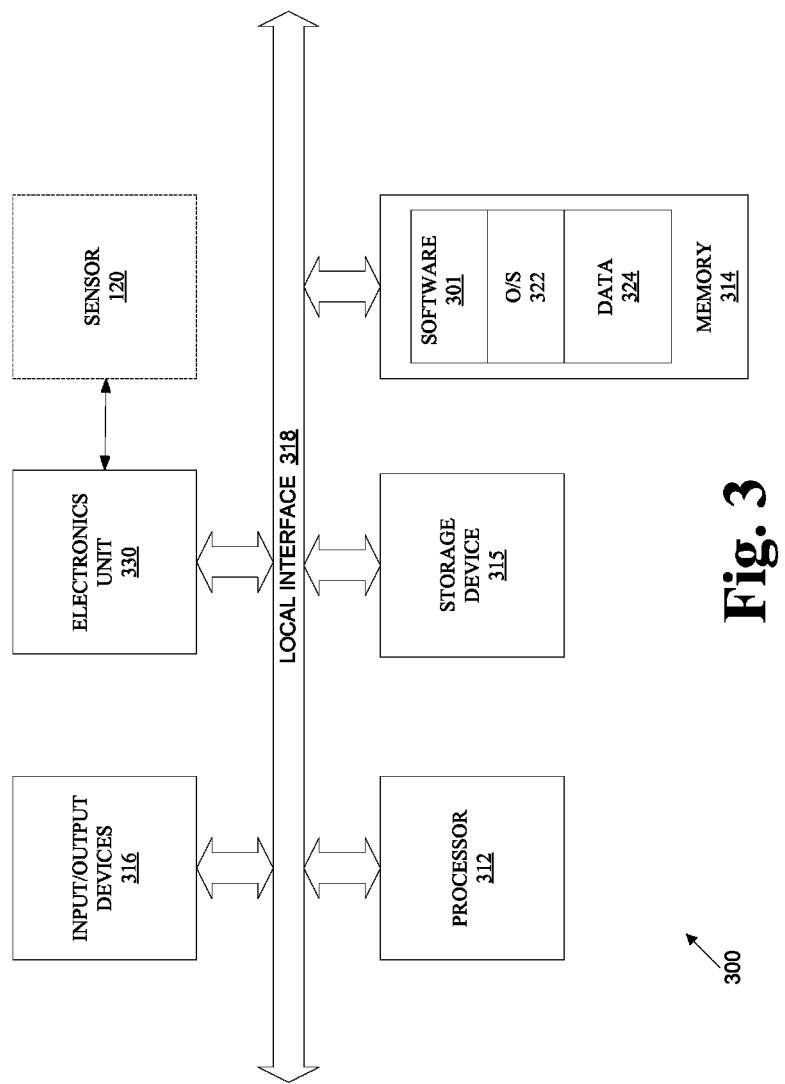
FIG. 3 is a schematic diagram showing an example of a fluid monitoring computer and associated software for implementing a method for time domain reflectometric fluid identification and quality monitoring within a vessel.

An example of a general purpose computer that can perform functionality of the fluid monitoring system of the present invention is shown in FIG. 3. In FIG. 3, the fluid monitoring system is denoted by reference numeral 300. It should be noted that communication with the fluid monitoring system may be provided by multiple means such as, but not limited to, the Internet. Note that where the description below refers to a system for time domain reflectometric measurement of fluid characteristics within a tank in accordance with one aspect of the present invention, this description should be understood to apply as well to a method for time domain reflectometric measurement of fluid characteristics within a tank in accordance with another aspect of the present invention with modification as appropriate. The present system may be provided by a Web-based application. The following description assumes that the present system is provided by a Web-based application. It should be noted that the system may also be provided in an environment that is not Web-based.

The fluid monitoring system of the invention can be implemented in software, firmware, hardware, or a combination thereof. In the current example, the fluid monitoring system is implemented in software, as an executable program, and is executed by a special or general purpose digital computer, such as a personal computer (PC; IBM-compatible, Apple-compatible, or otherwise), workstation, minicomputer, digital signal processor (DSP), microcontroller, or mainframe computer. Specifically, the fluid monitoring system, as provided by the computer, may be accessible via a Web site, through which parties using the fluid monitoring system may interact. Further description of the fluid monitoring system, and interaction therewith is provided below.

Generally, in terms of hardware architecture, as shown in FIG. 3, the computer 300 includes an electronics unit 330, a processor 312, memory 314, storage device 315, and one or more input and/or output (I/O) devices 316 (or peripherals) that are communicatively coupled via a local interface 318. The local interface 318 can be, for example but not limited to, one or more buses or other wired or wireless connections, as is known in the art. The local interface 318 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

FIG. 3 also depicts the sensor 120 as per FIG. 1. The sensor 120, while not part of the computer system 300, is included in FIG. 3 to assist in understanding how the elements of the computer system 300 relates to the TDR fluid sensing system 100 of FIG. 1. The sensor 120 includes a transmitter and a receiver.

The processor 312 is a hardware device for executing software, particularly that stored in the memory 314. The processor 312 can be any custom made or commercially available processor, a central processing unit (CPU), an auxiliary processor among several processors associated with the computer 300, a semiconductor based microprocessor (in the form of a microchip or chip set), a macroprocessor, or generally any device for executing software instructions.

The memory 314 can include any one or combination of volatile memory elements (for example, random access memory (RAM, such as DRAM, SRAM, SDRAM, etc.)) and nonvolatile memory elements (such as ROM, hard drive, tape, CDROM, etc.). Moreover, the memory 314 may incorporate electronic, magnetic, optical, and/or other types of storage media. Note that the memory 314 can have a distributed architecture, where various components are situated remotely from one another, but can be accessed by the processor 312.

The software 301 in memory 314 may include one or more separate programs, each of which comprises an ordered listing of executable instructions for implementing logical functions of the fluid monitoring system, as described below. In the example of FIG. 3, the software 301 in the memory 314 defines the fluid monitoring system functionality in accordance with one embodiment of the present invention. In addition, the memory 314 may contain an operating system (O/S) 322. The operating system 322 essentially controls the execution of computer programs and provides scheduling, input-output control, file and data management, memory management, and communication control and related services.

Instructions for implementing the fluid monitoring system 300 may be provided by a source program, executable program (object code), script, or any other entity comprising a set of instructions to be performed. A source program is typically translated via a compiler, assembler, interpreter, or the like, which may or may not be included within the memory 314, so as to operate properly in connection with the O/S 322. Furthermore, instructions for implementing the fluid monitoring system 300 can be written as (a) an object oriented programming language, which has classes of data and methods, or (b) a procedure programming language, which has routines, subroutines, and/or functions.

The memory 314 may also be used to store data 324, such as reference characteristics of known fluids, or ranges of fluid characteristics that may, for example, identify when contaminants or additives in a fluid are within acceptable operational levels. This data may be stored in non-volatile memory, or may be stored in volatile memory, allowing a system operator to update or modify the data as desired.

The I/O devices 316 may include input devices, for example but not limited to, a keyboard, mouse, scanner, microphone, or other input device. Furthermore, the I/O devices 316 may also include output devices, for example but not limited to, a printer, display, or other output device. Finally, the I/O devices 316 may further include devices that communicate via both inputs and outputs, for instance but not limited to, a modulator/demodulator (modem; for accessing another device, system, or network), a radio frequency (RF) or other transceiver, a telephonic interface, a bridge, a router, or other device.

When the fluid monitoring system 300 is in operation, the processor 312 is configured to execute the software 301 stored within the memory 314, to communicate data to and from the memory 314, and to generally control operations of the computer 300 pursuant to the software 301. The fluid monitoring system 300 and the O/S 322, in whole or in part, but typically the latter, are read by the processor 312, perhaps buffered within the processor 312, and then executed.

When the fluid monitoring system 300 is implemented in software, as is shown in FIG. 3, it should be noted that instructions for implementing the fluid monitoring system 300 can be stored on any computer-readable medium for use by or in connection with any computer-related system or method. Such a computer-readable medium may, in some embodiments, correspond to either, or both, of the memory 314 or the storage device 315 shown in FIG. 3. Instructions for implementing the fluid monitoring system 300 can be embodied in any computer-readable medium for use by or in connection with the processor 312 or other such instruction execution system, apparatus, or device. Although the processor 312 has been mentioned by way of example, such instruction execution system, apparatus, or device may, in some embodiments, be any computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the processor 312 or other such instruction execution system, apparatus, or device. Such a computer-readable medium may be, for example but not limited to, an electronic, magnetic, optical, electromagnetic, infrared, or semiconductor system, apparatus, device, or propagation medium, or other physical device or means that can contain or store a computer program for use by or in connection with a computer-related system or method. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the fluid monitoring system 300 is implemented in hardware, the fluid monitoring system 300 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Identifying a Fluid by Comparing a Derived Characteristic of a Fluid to a Reference Characteristic As mentioned above, a capacitance probe is ill suited for measuring properties of two or more stratified fluid layers, as it would return indeterminate results across a fluid boundary. In contrast, TDR may detect stratified layers of fluids within a vessel, an example of which is shown by copending U.S. nonprovisional patent application entitled "System and Method for Optimizing Sweep Delay And Aliasing For Time Domain Reflectometric Measurement of Liquid Height Within A Tank," having Ser. No. 12/630,305, filed Dec. 3, 2009, which is incorporated herein in its entirety. There are many applications where it is desirable to both detect the presence of stratified layers, and to determine the identity of a stratified fluid layer. Since, for example, water may enter a vessel such as a fuel tank in sufficient amounts to form its own layer, it may be advantageous to both detect the boundaries of the water layer, and to identify the layer as water.

Figure 4:
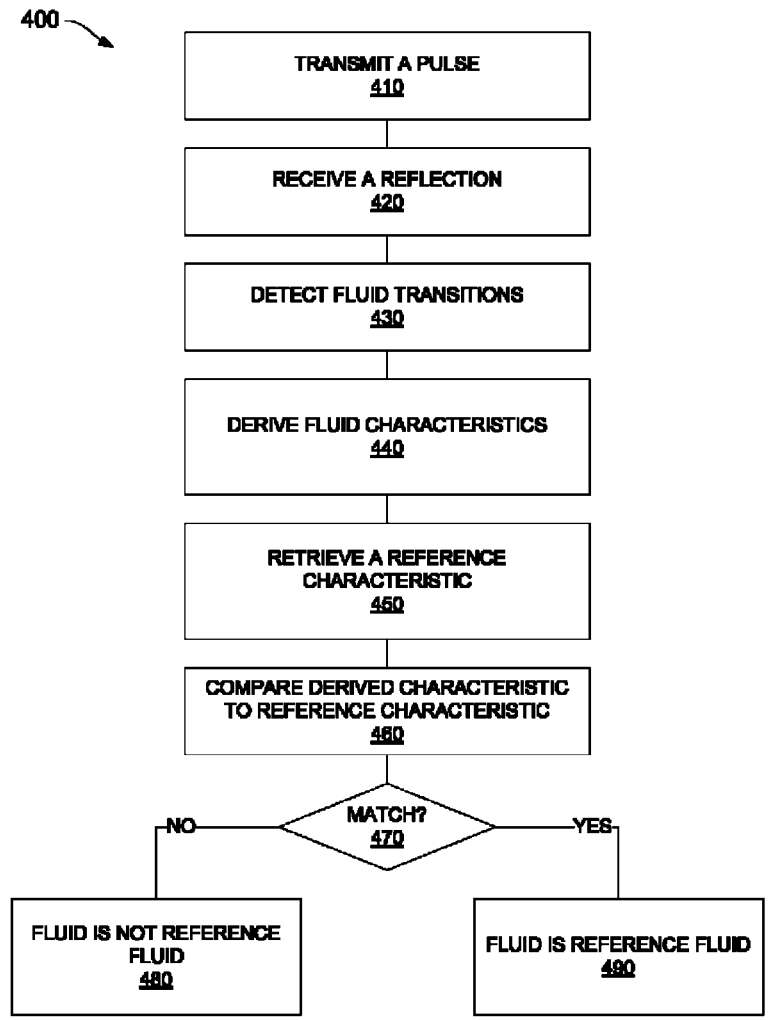
FIG. 4 is a flowchart illustrating a first embodiment of a method for identifying a fluid using TDR.

FIG. 4 is a flow chart 400 depicting a first embodiment of a method of identifying a fluid using TDR. As shown by block 410, an interrogation pulse is transmitted into a subject fluid to be identified. As shown by block 420, a reflection of the interrogation pulse off one or more transition boundary is received. As shown by block 430, the transition boundaries are detected using TDR analysis techniques described above. A fluid characteristic of the subject fluid is then derived (block 440). Some examples of derived fluid characteristics include, but are not limited to, permittivity, velocity of propagation, or impedance.

As shown by block 450, a reference characteristic is retrieved from memory. The reference characteristic is of the same type as the characteristic derived for the subject fluid, but it is the characteristic of a known fluid, where the known fluid is typically in a pure, uncontaminated state. As shown by block 460, the derived characteristic of the subject fluid is compared with the reference characteristic. Note, that in order for this comparison to be meaningful, the reference characteristic may be selected as a function of the temperature or density of the subject fluid. For example, if the subject fluid was tested at room temperature, and the derived characteristic is impedance, then the reference characteristic may be the impedance of the reference fluid at room temperature. This is because many characteristics vary with temperature and/or density, so a comparison between derived and reference characteristics may take temperature and/or density into consideration.

As shown by block 470, it is determined whether the derived characteristic and the reference characteristic match. In some instances, a match may require that the derived characteristic and the reference characteristic are identical. In other instances, a match may be declared if the derived characteristic is nearly identical, that is, within a defined range either above or below the reference characteristic. A discussion regarding acceptable ranges follows. If a match is found (block 470), the fluid is declared to be the same as the reference fluid (block 490). Otherwise, as shown by block 480, the fluid remains unidentified.

A Dielectric Constant Table

An example of the first embodiment of a method identifying a fluid is using a dielectric constant table as a reference for a dielectric constant derived for a subject fluid using TDR. Such a dielectric constant table may be located, for example, in memory 314 (FIG. 3). The dielectric table may contain the dielectric constants of several fluids as a function of temperature. So for this example block 450 might entail using the dielectric constant table to look up a calculated dielectric constant of a fluid at the temperature of the fluid when tested. The table may be restricted to fluids expected to be present in the vessel. The dielectric constant provided for each fluid in the table may typically represent the dielectric constant of that fluid when uncontaminated. Since impurities or contamination may change the dielectric constant of a fluid, each table entry may also contain configurable offset values representing both an acceptable low range for the dielectric constant and an acceptable high range for the dielectric constant. For example, if a first fluid having dielectric constant, a, is mixed with a contaminating second fluid having dielectric constant b, where a>b, the measured dielectric constant of the mixture will be less than a. On the other hand, if the first fluid is mixed with a third fluid having a dielectric constant c, where a<c, the dielectric constant of the mixture will be greater than a. In both cases, the divergence between the pure value a and the calculated value will depend upon the differences in dielectric constant values of the two fluids, the relative proportions of each fluid in the mixture, and the temperature of the fluids when measured.

The acceptable low range floor and the acceptable high range ceiling for each fluid is configurable based upon several factors. Some variation between the ideal value and the measured value may be considered normal. For instance, fuels may contain additives, such as antifreeze or anti-rust agents. The acceptable low and high ranges may take the presence of acceptable levels of such additives into account. In addition, minimal levels of other contaminants, such as water in fuel, may not cause a degradation of performance. Therefore, the dielectric constant table factors in the presence of acceptable amounts of additives and contaminants.

The dielectric constant table may be used to identify a fluid as follows. The TDR system detects two boundary transitions, and calculates the dielectric constant of the fluid corresponding to the fluid between the two boundaries. The calculated dielectric constant is compared to values in the dielectric constant table. That is, if the calculated dielectric constant falls below the table entry high value and above the table value low range value for a material, the table search function returns a successful match. The dielectric constant table may contain entries for more than one state of a fluid. For example, water ice has a lower dielectric constant than liquid water, but still much larger than liquid fuel. Therefore, a reference dielectric constant table may have one entry for identifying liquid water, and another entry for identifying water ice.

While a dielectric constant table may contain entries for a large number of fluids, there may be situations where it is advantageous to limit the number of entries. The expected contents of the fuel tank may be useful for creating the dielectric constant table. For example, if the application is detecting contents of a general aviation aircraft fuel tank, the dielectric table may only contain entries for air, avgas, water ice and liquid water. There would be no need to include an entry for jet fuel in the dielectric constant table. Similarly, the high and low range values for avgas in the table would be most effective if they reflect values corresponding to acceptable levels of additives, or tolerable levels of contaminants.

While the above example used the dielectric constant as an example of a reference characteristic, other reference characteristics are also suitable for identifying a fluid using TDR. Examples of other suitable reference characteristics of a fluid include, but are not limited to, the reflection coefficient, impedance, and propagation velocity. But since the propagation time of an interrogation pulse through a medium is directly proportional to the dielectric constant of a fluid, a similar fluid identification process can be performed without having to calculate the dielectric constant of the fluid. Instead of a table of dielectric constants, the table can contain propagation velocities of various fluids, and corresponding high and low range values based upon acceptable levels of additives or contaminants.

Monitoring Fluid Quality

TDR may use two or more measured parameters, such as temperature and layer height to derive another characteristic of the fluid, such as the dielectric constant. As described above, the dielectric constant lookup table may be used to determine the identity of a fluid if the fluid is unknown. If the identity of the fluid is known, reference characteristics of the known fluid may be compared with derived characteristics of the previously identified fluid to detect conditions where the fluid may be unsuitable for its intended application. For example, the dielectric constant of fuel changes with impurities, such as water or microbial growths, and similarly changes upon the introduction of ethanol or alcohol based additives such as antifreeze or rust inhibitors. High levels of certain contaminants or additives in fuel may cause a drop in engine power, or cause the engine to malfunction. Since the proportion of the various impurities or additives may be unknown and since two or more additives and contaminants may be simultaneously present, the identity of the impurities may be difficult to ascertain. Even so, monitoring fluid quality with TDR may determine whether the fluid is within operational tolerances, even if the identity of the contaminating agent cannot be determined. Similarly, while the presence of water and fuel mixture may be detected, it may be difficult to discern whether the water is dissolved, emulsified, or a combination of the two.

Figure 5:
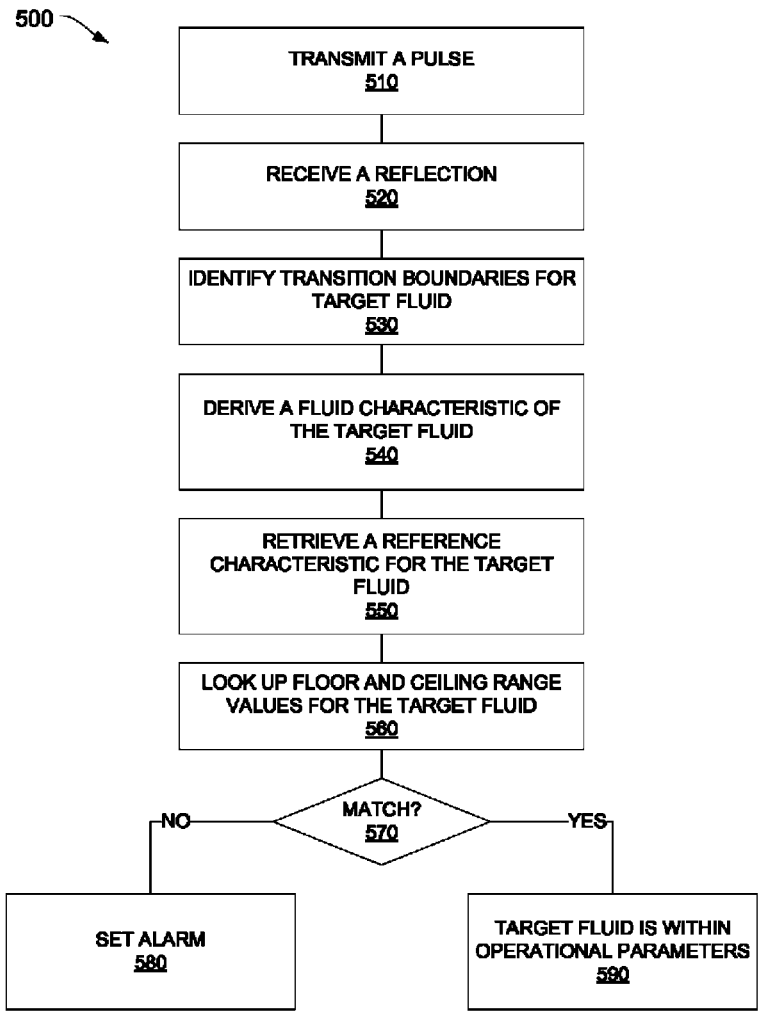
FIG. 5 is a flowchart illustrating a second embodiment of a method for using TDR to monitor fluid quality.

A second embodiment of a method to use TDR to monitor fluid quality is shown by the flow chart 500 of FIG. 5. As shown by block 510, an interrogation pulse is transmitted into a target fluid being monitored. A reflection of the interrogation pulse off of the transition boundaries of the target fluid is received (block 520). As shown by block 530, the target fluid transition boundaries are identified using TDR analysis techniques described above. As shown by block 540, a fluid characteristic of the target fluid is derived. Examples of derived fluid characteristics include, but are not limited to, permittivity, velocity of propagation, or impedance. As shown by block 550, a reference characteristic of the target fluid is retrieved from memory. A floor value and a ceiling value of a quality range of the target fluid is retrieved from memory (block 560). As before, this range may be adjusted based upon the known parameters of the target fluid, for example, the temperature of the target fluid, or the temperature of the target fluid as measured, for example, by a densitometer.

As shown by block 570, it is determined whether the derived characteristic of the subject fluid is within the quality range. If the subject fluid is in range (block 590), the process is finished. If the derived characteristic of the subject value is out of range (block 580), an alarm is raised. The alarm may be a signal, such as an audible alarm or lit alarm indicator, or may be an electrical or computer generated message indicating that the monitored fluid is outside expected tolerances. Note that in some embodiments, the alarm may not be raised until multiple successive measurements indicate that the quality of the fluid is out of range. Still other embodiments may use a smoothing filter, so that the target fluid must be measured to be out of range more often than not over a measurement window. These and other techniques may be used by a person having ordinary skill in the art to avoid triggering an out of range alarm caused by spurious or anomalous readings.

The floor and ceiling range value of a reference fluid may also be modified. For instance, the acceptable range of avgas may be set to broader bounds when certain additives, such as antifreeze, are known to be in use. Another application for the second embodiment is to detect misfueling (that is, when a tank has inadvertently been filled with the wrong fuel). For example, if a fuel is tested using the second embodiment immediately after refueling and is measured as outside of acceptable range, misfueling may be indicated.

Monitoring a Fluid for a Dynamic Change in Quality

Figure 6:
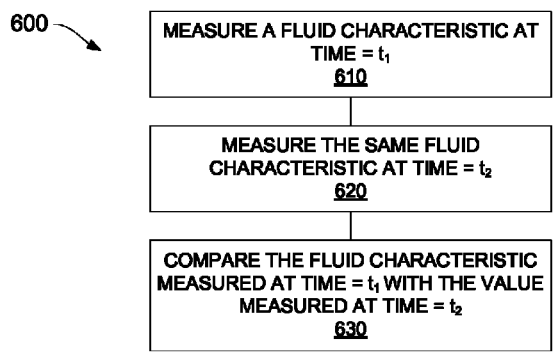
FIG. 6 is a flowchart illustrating a third embodiment of the invention where TDR detects conditions within a vessel as they change over time.

TDR may also be used to detect changing conditions within a vessel as they occur. A third embodiment of the invention is a method used to monitor fluid changes with TDR. A flow chart 600 illustrating the method of the third embodiment is shown by FIG. 6. A fluid characteristic is measured with TDR at a first time, $t_1$ (block 610). As with the second embodiment, the fluid is assumed to be known at the time of the first measurement, and the fluid characteristic may be either directly measured or derived. Such characteristics include, but are not limited to, dielectric constant, permittivity, reflective coefficient, and propagation velocity. The same characteristic of the same fluid is measured at a second time $t_2$, where $t_2$ is later than $t_1$ (block 620). The fluid characteristic measured at the first time is compared to the fluid characteristic measured at the second time (block 630).

In some cases, in order for the comparison of the fluid at $t_1$ to the fluid at $t_2$ to be meaningful, the two compared characteristics should be normalized with respect to the temperature at which they were taken. If the temperature is different at the first time than at the second time, a difference in the fluid characteristics would be unremarkable. However, if the characteristics are normalized with respect to a reference temperature, then a difference between the two measurements may be the result of a change that may be noteworthy. Similarly, the normalization may be calculated in reference to other known parameters, for example, the density of the fluid as measured by, for example, a densitometer.

Continuing with the general aviation example, consider the case where an aircraft fuel tank initially contains only air and avgas. Since the aircraft was fueled in an area of high humidity, water vapor was introduced to the air in the fuel tank. As the temperature drops, the water vapor condenses, and a layer of liquid water forms in the tank. The TDR system could detect the formation of this layer of water by new transition reflections at the top and bottom of the water layer. Then the layer could be identified as water using the first embodiment as described above.

A second example of dynamic changes in a general aviation craft fuel tank is if the water vapor of the previous example, instead of separating out as a water layer, instead mixed with the fuel as emulsified water. This would effectively raise the dielectric constant of the fuel layer, and this change can be monitored using the third embodiment, as described above.

A third example of dynamic changes in a general aviation craft fuel tank is if the temperature dropped in the second example, causing the emulsified water to begin to freeze. Since the dielectric constant of liquid water is higher than the dielectric constant of water ice, the calculated dielectric constant of the fuel layer would begin to drop. Again, this change can be monitored by the TDR system using the third embodiment. Observing changes over time in the reflected TDR waveform may provide additional information regarding conditions within the fuel tank. The falling dielectric constant in a fuel layer may be caused, for example, by the emulsified water settling out and forming a liquid water level.

Figure 7:
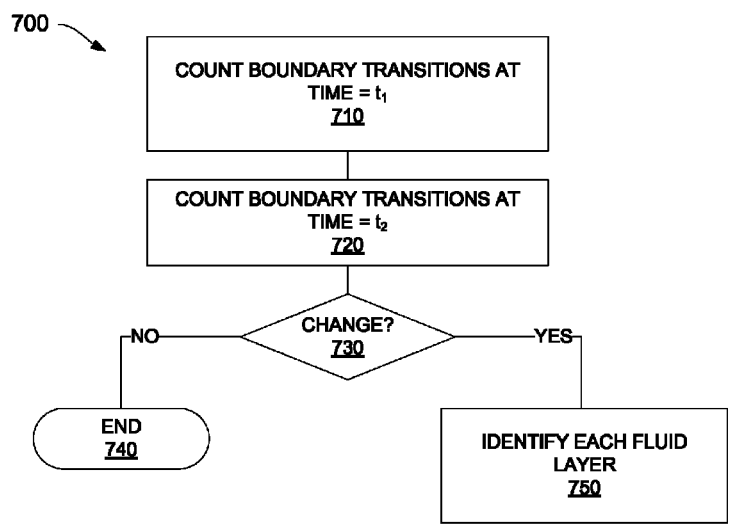
FIG. 7 is a flowchart of a method under the third embodiment to detect a change in the number of detected boundary transitions over time.

The characteristics compared at block 630 of FIG. 6 may include the dielectric constant, the propagation velocity, the impedance, or other characteristics of a single fluid measured at two times. Alternatively, the fluid characteristic compared at block 630 may include the number of boundary transitions detected. FIG. 7 is a flowchart 700 of a method to detect a change in the number of detected boundary transitions over time, which may indicate, for example, the formation of a new fluid layer in a vessel. As shown by block 710, the number of boundary transitions is counted at a first time $t_1$. As shown by block 720, the number of boundary transitions is counted at a second time $t_2$. A change in the number of boundary conditions is detected (block 730), which entails comparing the number of boundary transitions detected at $t_1$ with the number of boundary transitions detected at $t_2$. If there is no change detected, the process ends (block 740). If a change is detected, each fluid layer is identified (block 750), for example, using the first embodiment as described above.

Returning to the third example, a newly formed liquid water level may be detected as per the flow chart 700 and identified with TDR as described in the first embodiment. On the other hand, a falling dielectric constant that is not accompanied by the detection of a liquid water layer may indicate the formation of ice or a fuel-ice gel in the fuel layer. Therefore, the third embodiment may be used both to monitor changes in an existing layer, and also to detect the formation of a new layer by detecting the additional boundary transitions as the new layer forms over time. Upon detection of the new layer, the fluid of the new layer may be identified using the first embodiment, as per above, or by a fourth embodiment, discussed below under the subheading, "Identifying a fluid by comparing a transition reflection waveform to a signature transition."

The discussion of FIG. 7 has thus far concentrated on the appearance of a new layer. However, there may be scenarios where the number of boundary transitions at block 730 decreases. This may indicate, for example, that water that previously formed its own fluid layer has become mixed with a fuel layer, perhaps in emulsified form caused by agitation of a fuel tank. Under such a scenario, block 750 would entail identifying each detected fluid layer, such as with the method of the first embodiment. It should be noted that the emulsified water in the fuel would significantly change the properties of the fuel in comparison with the properties of a reference fuel that does not include emulsified water. Therefore, the identification of the layer of fuel containing emulsified water using the first embodiment may require taking into account the change in properties of the fuel caused by the emulsified water, such as accepting a dielectric constant significantly higher than a reference, unmixed fuel would have. Thus if at time $t_1$ an air layer, a fuel layer and a water level is detected, and at time $t_2$ an air layer is detected, but instead of detecting either a fuel layer or a water layer, these two layers are replaced by an unidentified layer with a dielectric constant above that of pure fuel and below that of pure water, it may be inferred that the identified layer is a mixture of fuel and water. This layer may then be tested as per the second embodiment to determine whether the water emulsion has caused the fuel to be contaminated beyond safe operational tolerances.

Identifying a Fluid by Comparing a Transition Reflection Waveform to a Signature Transition When an interrogation pulse traverses a boundary transition, the change in fluid properties across the boundary generates predictable and repeatable characteristics in the reflected signal according to the fluids on each side of the boundary transition. These characteristics, including, but not limited to phase, slope, and relative amplitude, together form a boundary transition signature. This boundary transition signature can indicate properties of the fluids on both sides of the transition. Furthermore, if the identity of a first fluid on one side of the boundary transition is known, the boundary transition signature may indicate one or more characteristics of the second fluid. The boundary transition signature may indicate a change of AC impedance between the first and second fluids. For example, changes in the phase and slope of the reflected signal immediately after boundary transition, and the relative amplitudes of the reflected signal after it has settled across the boundary transition may indicate whether the second fluid has a resistive, capacitive, or inductive load in comparison to the first fluid.

Figure 8:
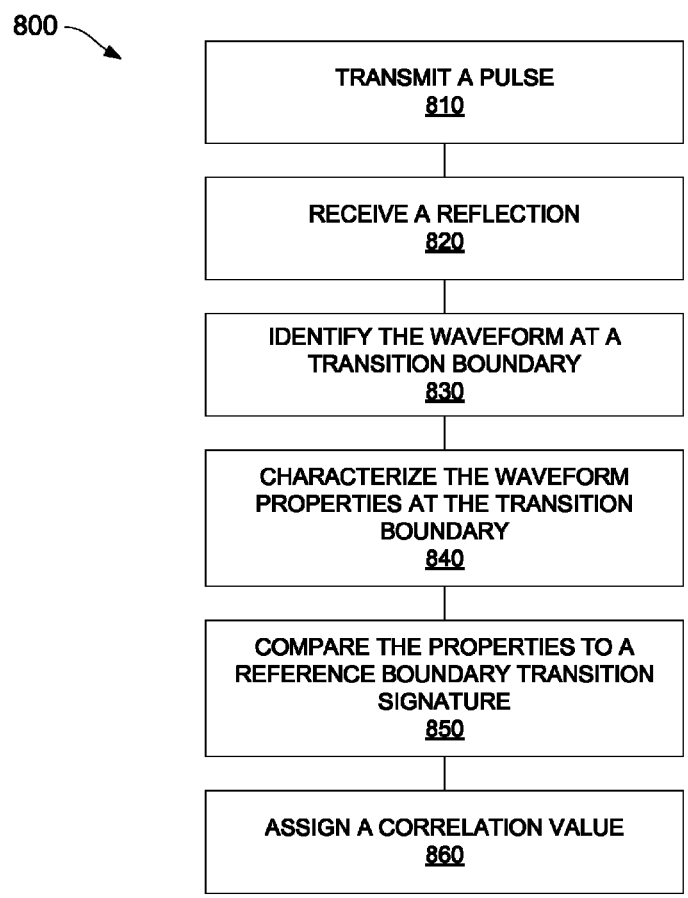
FIG. 8 is a flowchart of a method for using the signature of a reflected impulse from a transition boundary to identify one or more characteristics of a fluid.

A fourth embodiment of the current invention includes comparing the signature of a received reflected interrogation pulse at a boundary transition to a reference boundary transition signature. FIG. 8 is a flowchart 800 illustrating a method for using the signature of a reflected impulse from a transition boundary to identify one or more characteristics of a fluid. An interrogation pulse is transmitted (block 810), and a reflected waveform is received (block 820). The portion of the reflected waveform at a transition boundary is isolated (block 830). The properties of the waveform at the transition, such as phase change, amplitude overshoot, settled amplitude and time to settle, are then characterized (block 840). As shown by block 850, the characterized properties are compared to a reference boundary transition signature, which may be in a table of reference boundary transition signatures. A match or near match of the received signal to a boundary transition signature may be used to determine the identity of a fluid on one side of the boundary. Note that a reference boundary transition signature may include a stored waveform to be used for comparison, or may include individual parameters, for example, phase, slope and relative amplitude, that may be used to compare the received signature to a known signature across two fluids. The reference boundary transition signature may also contain both representations of stored waveforms and individual parameters.

Under the fourth embodiment, as the received reflected interrogation pulse is compared to a reference boundary transition signature, the pair may be assigned a correlation value (block 860). The correlation value indicates how closely the received reflected interrogation pulse matches the boundary transition signature table entry. For example, a pair having a high correlation value may indicate a better match than a pair having lower correlation value. The correlation value of the pairing may be compared to a threshold correlation value. If the correlation value of the pairing exceeds the threshold correlation value, a signature match is declared.

Similarly, examining the boundary transition signature may be used to determine fluid quality. Variations in the received signature with a stored signature may indicate the presence of impurities or additives in a fluid. Note that while a strong signature match may be used to identify a fluid, a weak signature match may not necessarily rule out identifying a fluid, as factors such as temperature or the presence of contaminants or additives may contribute to a reflected waveform not aligning with a reference boundary transition signature.

While the present invention has been described in connection with several embodiments thereof, it will be apparent to those skilled in the art that many changes and modifications may be made without departing from the true spirit and scope of the present invention. Accordingly, it is intended by the appended claims to cover all such changes and modifications as come within the true spirit and scope of the invention.

We claim:

1. A method of detecting the quality of a fluid in a vessel, comprising the steps of:
    transmitting an interrogation pulse into a vessel containing a fluid;
    receiving a first reflection of the interrogation pulse off of a first transition boundary;
    receiving a second reflection of the interrogation pulse off of a second transition boundary;
    measuring the time between receiving the first reflection and receiving the second reflection;
    determining a distance between the first transition boundary and the second transition boundary;
    calculating a derived characteristic of the fluid located between the first transition boundary and the second transition boundary based upon the distance between the first transition boundary and the second transition boundary and the time difference between receiving the first reflection and receiving the second reflection;
    determining a first configurable offset value to calculate a quality floor threshold;
    determining a second configurable offset value to calculate a quality ceiling threshold; and
    determining whether the derived characteristic is between the quality floor threshold and the quality ceiling threshold.

2. The method of detecting the quality of a fluid in a vessel of claim 1, wherein the steps of transmitting an interrogation pulse, receiving a first and second reflection of the interrogation pulse are performed using time domain reflectometry.

3. The method of detecting the quality of a fluid in a vessel of claim 2, wherein the step of setting the quality ceiling threshold is a function of the temperature of the fluid in the vessel, and the step of setting the quality floor threshold is a function of the temperature of the fluid in the vessel.

4. The method of detecting the quality of a fluid in a vessel of claim 3, wherein the derived characteristic of the fluid comprises the dielectric constant of the fluid.

5. The method of detecting the quality of a fluid in a vessel of claim 3, wherein the derived characteristic of the fluid comprises the propagation velocity of an electromagnetic pulse through the fluid.

6. The method of detecting the quality of a fluid in a vessel of claim 3, wherein the derived characteristic of the fluid comprises the impedance characteristics of the fluid.

7. The method of detecting the quality of a fluid in a vessel of claim 3, wherein the quality being detected comprises a level of contamination.

8. The method of detecting the quality of a fluid in a vessel of claim 7, wherein the contamination is emulsified water.

9. The method of detecting the quality of a fluid in a vessel of claim 3, wherein the quality being detected is the presence of misfueling.

10. The method of detecting the quality of a fluid in a vessel of claim 3, wherein the quality being detected is the presence of excessive additives.

11. A method of detecting a change in a fluid in a vessel, comprising the steps of:
measuring a fluid characteristic according to the method of claim 1 at a first time;
measuring the fluid characteristic according to the method of claim 1 at a second time, where the second time is after the first time; and
comparing the fluid characteristic measured at the first time to the fluid characteristic measured at the second time.

12. The method of detecting a change in a fluid in a vessel of claim 11, further comprising the steps of:
recording a first temperature of the fluid at the first time;
recording a second temperature of the fluid at the second time;
calculating a normalized fluid characteristic at the first time by adjusting the fluid characteristic at the first time in relation to a reference temperature;
calculating a normalized fluid characteristic at the second time by adjusting the fluid characteristic at the second time in relation to a reference temperature; and
comparing the normalized fluid characteristic at the first time to the normalized fluid characteristic at the second time.

13. A method of detecting a change in a fluid in a vessel, comprising the steps of:
measuring a fluid characteristic with TDR at a first time;
measuring the fluid characteristic with TDR at a second time, where the second time is after the first time; and
comparing the fluid characteristic measured at the first time to the fluid characteristic measured at the second time,
wherein the fluid characteristic comprises the number of detected transition boundaries.

14. The method of detecting a change in a fluid in a vessel of claim 13, further comprising the step:
if the number of detected transition boundaries has changed, determining the identity of a fluid.

15. A system for monitoring the quality of a fluid in a vessel, comprising:
a transmitter configured to transmit an interrogation pulse into the vessel;
a receiver, configured to receive reflected portions of the interrogation pulse;
an electronics unit in communication with said transmitter and said receiver, the electronics unit cyclically transmitting interrogation pulses to the transmitter and receiving reflections from the receiver for time domain reflectometric measurement of the fluid;
a memory; and
a processor in communication with the electronics unit and the memory, the processor configured by the memory to perform steps comprising:
detecting first and second impedance transitions corresponding to first and second boundaries of a bounded region of known length;
calculating a derived characteristic of the fluid located between the first boundary and the second boundary;
determining a first configurable offset value to calculate a quality floor threshold;
determining a second configurable offset value to calculate a quality ceiling threshold; and
determining whether the derived characteristic is between the quality floor threshold and the quality ceiling threshold.

* * * * *